(12) United States Patent
Proelss et al.

(10) Patent No.: US 9,931,524 B2
(45) Date of Patent: Apr. 3, 2018

(54) METAL EFFECT PIGMENT WITH ADDITIVE

(75) Inventors: Dieter Proelss, Schwabach (DE); Stefan Trummer, Nürnberg (DE); Stephan Roth, Bayreuth (DE); Bärbel Gertzen, Emmerich (DE); Wolfgang Pritschins, Wesel (DE); Jürgen Omeis, Dorsten-Lembeck (DE)

(73) Assignee: ECKART GMBH (DE)

( * ) Notice: Subject to any disclaimer, the term of this patent is extended or adjusted under 35 U.S.C. 154(b) by 502 days.

(21) Appl. No.: 12/994,879

(22) PCT Filed: May 28, 2009

(86) PCT No.: PCT/EP2009/003824
§ 371 (c)(1),
(2), (4) Date: Dec. 13, 2010

(87) PCT Pub. No.: WO2009/144023
PCT Pub. Date: Dec. 3, 2009

(65) Prior Publication Data
US 2011/0094412 A1 Apr. 28, 2011

(30) Foreign Application Priority Data
May 28, 2008 (EP) .................... 08009700

(51) Int. Cl.
| *A61Q 19/00* | (2006.01) |
| *A61K 8/11* | (2006.01) |
| *A61K 8/86* | (2006.01) |
| *C09D 5/36* | (2006.01) |
| *C09C 1/66* | (2006.01) |
| *C09C 1/64* | (2006.01) |
| *A61K 8/39* | (2006.01) |
| *C09C 1/62* | (2006.01) |
| *C09D 7/12* | (2006.01) |
| *C08K 3/08* | (2006.01) |
| *C08K 9/04* | (2006.01) |

(52) U.S. Cl.
CPC ............... *A61Q 19/00* (2013.01); *A61K 8/11* (2013.01); *A61K 8/39* (2013.01); *A61K 8/86* (2013.01); *C09C 1/62* (2013.01); *C09C 1/622* (2013.01); *C09C 1/625* (2013.01); *C09C 1/646* (2013.01); *C09C 1/66* (2013.01); *C09D 5/36* (2013.01); *C09D 7/1225* (2013.01); *A61K 2800/412* (2013.01); *A61K 2800/413* (2013.01); *A61K 2800/43* (2013.01); *C01P 2004/54* (2013.01); *C01P 2004/61* (2013.01); *C01P 2004/86* (2013.01); *C01P 2006/60* (2013.01); *C01P 2006/62* (2013.01); *C01P 2006/63* (2013.01); *C01P 2006/64* (2013.01); *C01P 2006/65* (2013.01); *C01P 2006/66* (2013.01); *C08K 3/08* (2013.01); *C08K 9/04* (2013.01)

(58) Field of Classification Search
CPC . A61Q 19/00; A61K 8/11; A61K 8/86; A61K 8/39; C09D 5/36; C09D 7/1225; C09C 1/66; C09C 1/646; C09C 1/625; C09C 1/622; C01P 2006/62; C01P 2006/64; C01P 2006/65; C01P 2006/66; C01P 2006/60; C01P 2004/61; C01P 2004/54; C01P 2006/63; C08K 3/08; C08K 9/04; A61L 2800/43; A61L 2800/413; A61L 2800/412
See application file for complete search history.

(56) References Cited

U.S. PATENT DOCUMENTS

| 3,551,174 | A | 12/1970 | Hauska et al. | |
| 3,857,865 | A | 12/1974 | Sturwold | |
| 4,484,951 | A | 11/1984 | Uchimura | |
| 4,629,512 | A | 12/1986 | Kondis | |
| 6,267,810 | B1 * | 7/2001 | Pfaff et al. | 106/415 |
| 6,398,861 | B1 * | 6/2002 | Knox | 106/404 |
| 6,761,762 | B1 | 7/2004 | Greiwe et al. | |
| 7,151,153 | B2 | 12/2006 | Bruchmann et al. | |
| 7,205,351 | B2 | 4/2007 | Pritschins | |
| 7,511,085 | B2 | 3/2009 | Bruchmann et al. | |
| 2007/0022901 | A1 | 2/2007 | Kurze et al. | |
| 2007/0051272 | A1 | 3/2007 | Wheeler | |
| 2007/0199478 | A1 | 8/2007 | Schlegl et al. | |
| 2008/0087187 | A1 | 4/2008 | Maul et al. | |
| 2008/0306167 | A1 | 12/2008 | Morvan | |
| 2009/0264575 | A1 | 10/2009 | Henglein et al. | |
| 2011/0094412 | A1 | 4/2011 | Proelss et al. | |

FOREIGN PATENT DOCUMENTS

| DE | 2436902 | 2/1975 |
| DE | 3002175 | 7/1980 |
| DE | 202004005921 U1 | 7/2004 |
| DE | 10361437 A1 | 7/2005 |
| EP | 0240367 A | 10/1987 |
| EP | 0569907 A | 11/1993 |
| EP | 1304210 A1 | 4/2003 |

(Continued)

OTHER PUBLICATIONS

Dow: Carbowax Product Information, http://msdssearch.dow.com/PublishedLiteratureDOWCOM/dh_0865/0901b8038086527b.pdf?filepath=polyglycols/pdfs/noreg/118-01789.pdf&fromPage=GetDoc . Oct. 2011.*
European Office Action dated Jun. 27, 2011 in corresponding European Patent Application No. 09 753 678.3 (German language).

(Continued)

*Primary Examiner* — Nicole Buie-Hatcher
(74) *Attorney, Agent, or Firm* — Ostrolenk Faber LLP

(57) ABSTRACT

A metallic effect pigment with an additive, the additive being applied on at least a portion of the metallic effect pigment. The additive comprises, as structural units, at least one carboxylic acid having at least 4 carbon atoms and also at least one polyglycol ether. The carboxylic acid and the polyglycol ether are bonded covalently to one another. The disclosure is also directed to a method for producing these metallic effect pigments, and to the use thereof, as well as to a printing ink comprising the pigments.

24 Claims, No Drawings

(56) References Cited

FOREIGN PATENT DOCUMENTS

| EP | 1621586 A1 | 2/2006 |
|---|---|---|
| EP | 2 128 204 A1 | 12/2009 |
| FR | 1538456 A | 9/1968 |
| FR | 2064024 A | 7/1971 |
| JP | 56-166309 | 12/1981 |
| JP | 63-054475 | 3/1988 |
| JP | 09-272817 | 10/1997 |
| JP | 2000-234107 | 8/2000 |
| JP | 2003-055701 | 2/2003 |
| JP | 2003-253183 | 9/2003 |
| JP | 2007-204638 | 8/2007 |
| WO | WO 1998/17731 | 4/1998 |
| WO | WO 99/57204 | 11/1999 |
| WO | WO 02/36695 | 5/2002 |
| WO | WO 02/36697 | 5/2002 |
| WO | WO 2004/087816 A2 | 10/2004 |
| WO | WO 2006/070108 A1 | 7/2006 |

OTHER PUBLICATIONS

International Search Report dated Sep. 10, 2009, issued in corresponding international application No. PCT/EP2009/003824.
European Search Report dated Nov. 7, 2008, issued in corresponding priority European application No. EP 08009700.9.
Notice of Reasons for Rejection dated Feb. 5, 2013 in corresponding Japanese Patent Application No. 2011-510896 (with English language translation).
Peter Wiβling, Metallic Effect Pigments, Fundamentals and Applications, European Coatings Literature, pp. 14-17 (2006).

\* cited by examiner

METAL EFFECT PIGMENT WITH ADDITIVE

CROSS REFERENCE TO RELATED APPLICATIONS

The present application is a 35 U.S.C. § 371 National Phase conversion of PCT/EP2009/003824, filed May 28, 2009, which claims benefit of European Application No. 08009700.9, filed May 28, 2008, the disclosure of which is incorporated herein by reference. The PCT International Application was published in the German language.

TECHNICAL FIELD

The present invention relates to a metallic effect pigment with additive, to a method for producing it and to the use thereof, and also to a coating composition which comprises the metallic effect pigment with additive.

BACKGROUND

Metallic effect pigments are platelet-shaped metallic pigments which are distinguished by a particular metallic luster and color effects. The metallic effect pigments are used in paints, varnishes, printing inks, plastics, cosmetics, etc., since they allow production of particular optical effects, especially color effects and luster effects.

The metallic effect pigments are produced conventionally from atomized metal powder by grinding in ball mills. The metal powder required for this operation can be obtained by atomization of molten metal. In the course of the deformative grinding of the atomized metal powder, it is common to add lubricants in order to prevent cold welding of the metal particles to one another. Lubricants commonly used include oleic acid and stearic acid. Oleic acid produces non-leafing properties, stearic acid leafing properties, in the ground metallic effect pigments. Instead of these fatty acids it is of course also possible in each case to use higher or lower homologs as lubricants, such as palmitic acid, for example. Technical-grade fatty acids regularly consist of a mixture of a wide variety of homologous fatty acids, with a saturated fatty acid also always containing certain fractions of unsaturated fatty acids, and vice versa. In the practice of producing metallic effect pigments it is also usual to make use deliberately of mixtures of saturated and unsaturated fatty acids, in other words, for example, a mixture of stearic acid and oleic acid.

Particularly when unsaturated fatty acids are used as lubricating material, the problem arises of the shelf life of metallic effect pigments. The unsaturated fatty acids have a propensity toward polymerization. In the case of the pigments, which are stored mostly in the form of pigment paste or pigment powder, this results in irreversible agglomerations.

According to DE 30 02 175 it is also possible to use dicarboxylic acids as lubricants.

So that the metallic effect pigments have a particularly visually appealing effect in an application medium, as for example in a paint or an ink, it is necessary for the metallic effect pigments to be oriented largely plane-parallel in the application medium, in order to provide directed reflection of the incident light. A random orientation of the metallic effect pigments in the application medium produces an undirected reflection of incident light in all directions, which for a viewer results in a low-grade visual impression.

In an application medium, such as a paint or an ink, for example, metallic effect pigments constitute an alien body or a disruption, which can lead to impaired mechanical properties, on the part of the dried ink or cured paint, for example. These impaired mechanical properties are manifested, for example, in low abrasion resistance, low stability toward environmental effects such as heat, cold, moisture etc. There may also be a splitting of a printing-ink or paint film along the plane in which the metallic effect pigments are oriented, resulting hence in extensive delamination.

WO 99/57204 discloses effect pigments coated with surface modifiers. These surface modifiers have a first reactive functional group which binds to the pigment surface and at least one second reactive functional group which is different from the first functional group and which binds, for example, to the binder system of a paint or of an ink. Although this surface modification increases the mechanical stability of a paint coat or of an ink film, this chemical surface modification has to be carried out in a separate step, which is time-consuming and costly.

DE 24 36 902 discloses an ester composition which comprises polyoxyalkylene glycol groups, monofunctional alcohol groups, and a dibasic acid, the ester having an acid number of less than 25 and a hydroxyl number of less than 25, and comprising 2% to 40% by weight of polyoxyalkylene glycol groups. This ester composition is used in the form of an emulsion with water as a lubricant in the machining of ferrous and nonferrous metals.

WO 2006/070108 A1 discloses a metal pigment composition produced with the metal particles being comminuted in the presence of a fatty acid ester R—COOR, where R is an alkyl radical having 1 to 8 C atoms.

WO 1998/17731 discloses a method for producing a low-dusting or non-dusting metallic effect pigment composition, the metal particles being ground in an aqueous liquid in the presence of corrosion inhibitors and a lubricant. Corrosion inhibitors which can be used include organic phosphorus compounds, examples being phosphate esters of long-chain ethoxylated alcohols.

EP 1 304 210 A1 discloses process auxiliaries for the processing of plastics masses. The process auxiliary comprises partial esters of polycarboxylic acids. The polycarboxylic acids may be dimer acids or trimer acids having 30 to 60 C atoms.

The prior art discloses lubricants or process auxiliaries for the machining or processing of metals or plastics, without any reference to production or use of metallic effect pigments.

The lubricants used to date in the production of metallic effect pigments do not make it possible, following incorporation of these metallic effect pigments into an application medium, to obtain a coating having improved mechanical properties, more particularly a lower splitability of ink layers or paint films, without prior costly and inconvenient surface modification of the metallic effect pigment surface.

SUMMARY

It is an object of the invention, therefore, to provide metallic effect pigments which are easy to produce, can be used subsequently in an application medium without costly and inconvenient reworking, and have an improved shelf life. The coatings obtained using the metallic effect pigmented application medium are to combine very good visual properties such as high gloss with improved mechanical properties.

The object on which the invention is based is achieved through provision of a metallic effect pigment with additive, the additive being applied at least partly on the metallic effect pigment and comprising as structural units at least one carboxylic acid having at least 4 carbon atoms and also at least one polyglycol ether, the carboxylic acid and the polyglycol ether being bonded covalently to one another.

Preferred developments of the metallic effect pigment of the invention are specified in dependent claims 2 to 12.

The object is further achieved through provision of a method for producing the metallic effect pigment of the invention, the method comprising the following steps:

a) grinding metal particles to metallic effect pigments in the presence of an additive which comprises as structural units at least one carboxylic acid having at least 4 carbon atoms, and also at least one polyglycol ether, the carboxylic acid and the polyglycol ether being bonded covalently to one another, and grinding media and also, optionally, a liquid phase, b) separating the metallic effect pigments obtained in step a) and provided with the additive from the grinding media and optionally from the liquid phase, c) optionally compacting the metallic effect pigments separated in step b) and provided with the additive.

Preferred developments of the method of the invention are specified in dependent claims 14 and 15.

The object is further achieved through the use of the metallic effect pigments of the invention for producing coating compositions, more particularly paints, coatings, printing inks, plastics or cosmetic formulations, and also through the provision of a coating composition comprising the metallic effect pigments of the invention.

DETAILED DESCRIPTION

By "structural units" is meant in accordance with the invention that the additive comprises a carboxylic acid having at least 4 carbon atoms. This carboxylic acid may be present as such or as a substituent, in the form of a side chain, for example. It is important that in any case the additive used has at least one structural unit in the form of a carboxylic acid having at least 4 carbon atoms.

The inventors have surprisingly found that the additive used in accordance with the invention results in improved shelf life of pastes or powders of the metallic effect pigments. Furthermore, the additive used in accordance with the invention results in improved mechanical stability of applied and dried and/or cured coating compositions which comprise the metallic effect pigments of the invention.

Furthermore it has emerged, surprisingly, that an additive which comprises as structural units at least one carboxylic acid having at least 4 carbon atoms and also at least one polyglycol ether, the carboxylic acid and the polyglycol ether being bonded covalently to one another, is outstandingly suitable as a lubricant which is needed in the production of the metallic effect pigments by mechanical grinding of metal particle, preferably atomized metal powder. Surprisingly it is possible for the metallic effect pigments obtained by mechanical deformation to be shaped into metal platelets having extremely low thicknesses, which exhibit high gloss and high brilliance.

In a likewise preferred embodiment, the additive is very suitable as a dispersing additive for metallic effect pigments. In this case it is with particular preference a metallic effect pigment paste and/or a metallic effect pigment filtercake to which this additive is added. Pastes of this kind feature significantly increased shelf life.

By an increased "shelf life" is meant that the metallic effect pigments exhibit no agglomeration or no substantial agglomeration in the course of storage. More particularly there is no agglomeration or no substantial agglomeration on storage of the metallic effect pigments of the invention in compressed form, more particularly as paste or as powder.

In one variant of the invention a significant fraction of the metallic effect pigment surface has the additive for use in accordance with the invention. In one preferred embodiment at least 30%, more preferably at least 50%, more preferably still at least 80%, more preferably still at least 90%, of the metallic effect pigment surface is provided with the additive for use in accordance with the invention.

Preferably 0.2% to 5% by weight of additive, more preferably 0.4% to 4% by weight, and very preferably 0.5% to 3% by weight of additive, based in each case on the amount of metallic effect pigment and additive, is bound on the surface of the metallic effect pigment.

The ratio of the additive to the metallic effect pigment is dependent in particular on the nature of the metal and on the specific surface area of the metal.

In order to be independent of this, the amount of additive (in ng) may also be represented as amount of additive per $cm^2$ of pigment surface area. In this case, preferably 10 to 3000 $ng/cm^2$, more preferably 30 to 2000 $ng/cm^2$, and very preferably 50 to 1000 $ng/cm^2$ of additive are bounded on the surface of the metallic effect pigment.

In the case of applications in the printing segment, a further advantage arises:

dispersing additives which are added to a printing ink comprising metallic effect pigments are commonly bound to a much lesser extent on the metal pigment surface. Frequently, however, the effect of this is disruptive, since many dispersing additives act as foam formers and therefore an undesirably large quantity of foam is produced when the metallic effect pigment is incorporated into the printing ink. The metallic effect pigments of the invention, in contrast, do not have this disadvantage, since in one preferred embodiment the additive is added during grinding itself and is therefore bound to the metallic effect pigment surface. Hence, when the metallic effect pigments of the invention are incorporated into a printing ink, the fraction of dispersing additive to be added separately can be reduced. In accordance with one preferred variant of the invention, there is no need at all for the additional use of dispersing additive in the printing ink.

Although it has not yet been established why the additive used in accordance with the invention on the one hand has very good lubricity in the mechanical grinding of atomized metal powder to metallic effect pigments, and on the other hand enables improved insertion or incorporation of the thus-produced metallic effect pigments in the application media, such as, paints, printing inks, varnishes, etc., it is supposed, without the inventors wishing to be tied to this supposition, that the very good lubricity is produced by the carboxylic acid having at least 4 carbon atoms together with the polyglycol ether.

It is further supposed that the lubricity is reinforced by a synergistic effect between carboxylic acid and polyglycol ether. It might be the case here that the covalent bonding of carboxylic acid and polyglycol ether produces an advantageous three-dimensional closeness, which might be important for very good lubricity on the part of the additive.

The good insertion or incorporation into an application medium and also the high shelf life might likewise be attributable to the simultaneous presence and the close three-dimensional coupling of carboxylic acid and polyglycol ether. In terms of character, the carboxylic acid(s) are hydrophobic molecules which have a great affinity for more apolar organic solvents. This is so particularly in the case of longer-chain carboxylic acids. In respect of the oxygen atoms that are present in the hydrocarbon chains, the polyglycol ethers are more polar in nature and therefore are hydrophilic molecules. They possess very good solubility in a large number of both polar and apolar solvents. In particular, they are highly water-soluble and are therefore often encountered in surfactants for aqueous applications. As a result of the combination of hydrophobic and hydrophilic properties, the metallic effect pigments of the invention are able to interact both with hydrophobic and with hydrophilic components of application media, which is why the metallic effect pigments of the invention are probably enveloped very effectively by paints, varnishes, printing inks, etc., and hence are inserted or incorporated into the application medium without acting as a substantial disruption or as an alien body. The good insertion or incorporation into the application medium might then result in the improved mechanical stability observed in a paint layer, varnish layer, printing ink layer, etc. These properties, surprisingly, apply both to water-based and to solvent-based application systems.

In accordance with one preferred development of the invention, the metals of the metallic effect pigments are selected from the group consisting of aluminum, copper, zinc, tin, gold bronze, iron, titanium, chromium, nickel, silver, gold, steel, and alloys thereof and mixtures of these metals.

Use is made very preferably of metallic effect pigments comprising or consisting of aluminum, iron, copper or gold bronze. Gold bronze here is brass, i.e. an alloy of copper and zinc.

The average thickness $h_{50}$ of the metallic effect pigments of the invention is situated preferably in a range from 15 nm to 5 µm, more preferably from 20 nm to 2 µm, more preferably still from 30 nm to 1 µm. A thickness range of 50 nm to 500 nm or of 70 nm to 150 nm has also proven very suitable.

In one particularly preferred embodiment, the metallic effect pigments are produced by grinding.

The metallic effect pigments of the invention may in principle be those known as "cornflakes" or else those known as "silver dollars". Cornflakes are metallic effect pigments which are obtained primarily by comminutive milling, and have frayed edges and a relatively rough surface. The silver dollar pigments, which are of higher optical quality, are obtained primarily by deformative grinding and have round edges and substantially smoother surfaces. For this reason they have fewer centers of scattering, resulting in increased luster and light-dark flop.

In recent years, further, very thin aluminum effect pigments have been described which increasingly are supposed to close the hitherto-existing gap between the visually very high-grade PVD pigments and the conventionally ground pigments on the other hand.

For instance, EP 1 621 586 A1 described aluminum pigments having thicknesses of 20 to 80 nm. WO 2004/087816 A2 describes aluminum pigments that are likewise thin, having average thicknesses of 30 to 100 nm, and having, moreover, a very smooth surface and a narrow thickness distribution of the pigments.

Entirely surprisingly, the metallic effect pigments of the invention, on account of the outstanding lubricity of the additive for use in accordance with the invention, can be shaped very easily down to very low pigment thicknesses. This is by no means confined to aluminum effect pigments; instead, very thin gold-bronze pigments or iron pigments can also be obtained.

In the case of aluminum, gold-bronze and/or iron effect pigments, preference is given in accordance with the invention to very thin metallic effect pigments having an average thickness $h_{50}$ of 15 to 100 nm, more preferably of 17 to 80 nm, and very preferably of 20 nm to 50 nm.

The average size of the metallic effect pigments is located preferably in a range from 1 µm to 200 µm, more preferably from 3 µm to 150 µm, and more preferably still from 5 µm to 100 µm.

The metallic effect pigments are platelet-shaped, and so the average size/thickness ratio (form factor) is preferably at least 5:1, more preferably at least 10:1, even more preferably at least 20:1, more preferably still at least 50:1. A size/thickness ratio of 100:1 or 1500:1 has also proven very suitable.

In another preferred embodiment, the metallic effect pigments are metallic effect pigments produced by means of the PVD method. Particularly preferred in this context are aluminum effect pigments in particular.

In the case of these embodiments, of course, the additive is used not as a lubricant, but is instead added preferably to the metallic effect pigment dispersion that is present.

The metallic effect pigments of the invention preferably possess a very high opacity as a result of the very low average thicknesses that are possible. Opacity of a pigment is typically identified as the masking of a surface area per unit weight of pigment amount. The thinner the average thickness of the metallic effect pigments, the greater the surface area masked by the pigment (per unit weight of the metallic effect pigment) and hence the opacity of the metallic effect pigment.

A low thickness, particularly in prints, is a very great advantage, since these prints, as compared for example to paint coatings, have a substantially lower thickness and a lower binder fraction.

The metallic effect pigments of the invention are very suitable, therefore, for use in printing inks. The effect of the additive for use in accordance with the invention is an improved insertion of the metallic effect pigment of the invention into the printed printing ink layer.

The metallic effect pigments of the invention are notable for extraordinary brilliance and an outstanding specific opacity. In printing applications in particular, brilliant hues are produced. In the case of aluminum effect pigments of the invention, for example, highly glossy silver-color coatings can be produced. Where brass or gold-bronze effect pigments of the invention are used, highly glossy gold-color coatings are produced.

When the metallic effect pigments are applied to films, such as polymeric films, in the form of reverse-face applications, films with extraordinary metallic brilliance are provided, particularly when viewed from the front face.

These reverse-face applications of the metallic effect pigments of the invention to film material are suitable in particular for flexible packaging, shrink-on films, laminates (to card, for example), packaging films, labels, in-mold decoration films in screen printing (for cell phone top shells, for example), etc.

The metallic effect pigments of the invention are preferably incorporated into printing inks and then printed on conventional printing machines onto paper, card, films, textiles, etc.

In one preferred embodiment the mechanical grinding of the metal particle in the presence of the additive for use in accordance with the invention applies the additive to the resultant metallic effect pigment surface. The additive may be bound to the metallic effect pigment surface by physical effects and/or by chemical bonding.

In accordance with one preferred embodiment, the metallic effect pigments of the invention are not coated further following mechanical grinding in the presence of the additive for use in accordance with the invention. The metallic effect pigments of the invention may therefore be incorporated directly into an application medium, where appropriate with a change in or removal of the solvent.

The metallic effect pigments of the invention can of course also be further coated, thus giving the metallic effect pigment surface an organic-chemical modification.

According to one preferred embodiment of the invention, the metallic effect pigments are non-leafing pigments. By non-leafing metallic effect pigments is meant that the metallic effect pigments arrange themselves not at or in the vicinity of the surface of an application medium, i.e., on the surface of the application medium that faces away from the substrate, as of a varnish, paint or printing-ink film, for example, but instead in the application medium. The metallic effect pigments of the invention are therefore enveloped by the application medium—binder, for example—and enclosed or incorporated in the course of drying or curing. The non-leafing metallic effect pigments of the invention are therefore already protected by the varnish, paint or printing ink from mechanical or chemical exposure.

It is of course also possible to apply a protective coat, such as a clearcoat, for example, to a coating with metallic effect pigments of the invention.

The metallic effect pigments of the invention can also be given leafing characteristics, as for example by additionally applying to the pigment surface saturated fatty acids having at least 12 C atoms, preferably palmitic acid or stearic acid.

The additive for use in accordance with the invention is obtainable by reaction of carboxylic acid and polyglycol ether.

This reaction of carboxylic acid and polyglycol ether takes place preferably by esterification and/or amidation.

Particularly preferred in this context is the covalent linking of polyglycol ether with the carboxylic acid by esterification. In this case the carboxylic acid functions are esterified wholly or at least partly with the polyglycol ether.

For example, carboxylic acid and polyglycol can be reacted with one another by conventional esterification reaction, as for example by temperature increase and water removal. The conditions of such esterification reactions are known to the skilled worker and are also described, for example, in EP 1 304 210 A1 or DE 24 36 902, hereby incorporated by reference.

The degrees of the esterification here are preferably 10% to 90%, more preferably 20% to 80%, and very preferably 25% to 75%.

Within these ranges a satisfactory balance is obtained between the hydrophobic and hydrophilic components of the additive.

According to another embodiment, the carboxylic acid is saturated or unsaturated. Saturated carboxylic acids are preferred here, however, since they result in a longer shelf life.

The carboxylic acid has preferably 6 to 130 carbon atoms, more preferably 8 to 100 carbon atoms, very preferably 10 to 96 carbon atoms, and with particular preference 20 to 80 carbon atoms. This number of carbon atoms relates to the hydrocarbon framework of the carboxylic acids, including the carboxylate functions, but not to the polyglycol ether units.

Below 4 carbon atoms in the carboxylic acid structural unit, preferably carboxylic acid or carboxylic acid radical, the advantageous effects of the additive in conjunction with the metal pigment are not discernible. Above 130 C atoms, the additive becomes increasingly insoluble in the majority of solvents. It is therefore difficult to synthesize and likewise barely still exhibits the advantageous effects in conjunction with the metallic effect pigment.

The carboxylic acid may be a monocarboxylic acid. Acids which have proven suitable in the context of the present invention as monocarboxylic acid having at least 4 carbon atoms which can be bonded covalently with polyglycol ether include saturated fatty acids. It is preferred to use fatty acids having 6 to 30 carbon atoms, more preferably having 10 to 24 carbon atoms, more preferably still having 14 to 22 carbon atoms. It is also possible to use mixtures of different monocarboxylic acids, in which case the values specified above for the number of carbon atoms should be understood as average values of the mixture of two or more monocarboxylic acids.

The fatty acids are preferably selected from the group consisting of valeric acid, caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotic acid, mellissic acid, and mixtures of these fatty acids.

As monocarboxylic acids having at least 4 carbon atoms it is also possible in accordance with the invention to use unsaturated fatty acids. It is preferred to use unsaturated fatty acids having 6 to 30 carbon atoms, more preferably having 10 to 24 carbon atoms, more preferably still having 14 to 22 carbon atoms.

The unsaturated fatty acids may be selected, for example, from the group consisting of undecylenic acid, palmitoleic acid, oleic acid, elaidic acid, vaccenic acid, eicosenoic acid, cetoleic acid, erucic acid, nervonic acid, sorbic acid, linoleic acid, linolenic acid, eleostearic acid, arachidonic acid, timnodonic acid, clupanodonic acid, docosahexaenoic acid, and mixtures of these fatty acids.

According to another preferred embodiment, carboxylic acids used include dicarboxylic acids, tricarboxylic acids, tetracarboxylic acids or mixtures thereof. As dicarboxylic and/or tricarboxylic acids which can be joined covalently with polyglycol ether it is likewise possible to use saturated and/or unsaturated carboxylic acids.

Dicarboxylic acids which can be used include, for example, succinic acid, glutaric acid, adipic acid, pimelic acid, suberic acid, azelaic acid and/or sebacic acid.

According to one particularly preferred development of the invention, dicarboxylic, tricarboxylic or tetracarboxylic acids with relatively long carbon frameworks are used. These dicarboxylic, tricarboxylic or tetracarboxylic acids are obtained preferably by di-, tri- or tetramerization of unsaturated fatty acids. The fatty acids used for this purpose have preferably 11 to 30 carbon atoms, more preferably 12 to 24 carbon atoms and more preferably still 14 to 22 carbon atoms. Examples of unsaturated fatty acids suitable for di-, tri- or tetramerization include oleic acid, linoleic acid, linolenic acid, eleostearic acid or similar acids. Although unbranched fatty acids are used with preference, it is of course also possible to use branched fatty acids.

Compounds of this kind are obtained as natural products and represent preferably mixtures of the monocarboxylic, dicarboxylic, tricarboxylic or tetracarboxylic acids or higher homologs. With particular preference the polycarboxylic acids are present predominantly in the form of the dicarboxylic acid.

Dicarboxylic acids having a carbon framework of 18 carbon atoms have proven very suitable. This dicarboxylic acid, accordingly, has 36 C atoms, and the corresponding tricarboxylic acid 54 C atoms.

The use of dicarboxylic acids in the reaction with polyglycol and/or polyglycol ether is preferred. Here there is preferably only partial esterification to give predominantly dicarboxylic acid monoglycol esters. A dicarboxylic acid monoglycol ester is able to bond to the metallic effect pigment surface via the free carboxylate group. This bond is preferably a covalent bond.

The polycarboxylic acid is preferably a monomeric, dimerized, trimerized or tetramerized fatty acid. For the fatty acids it is possible to use the fatty acids identified above, which are dimerized, trimerized or tetramerized. Mixtures of these different fatty acids are used with preference.

According to these preferred embodiments of the invention, the carboxylic acid is at least one polycarboxylic acid having two to eight carboxylic acid groups. With further preference the polycarboxylic acid comprises 2 to 4 carboxyl groups. These figures relate to the average values in the case of mixtures of any of a very wide variety of polycarboxylic acids.

It is further preferred for the polycarboxylic acid to contain 10 to 96, preferably 12 to 76, carbon atoms, more preferably 24 to 60 carbon atoms, more preferably still 36 to 54 carbon atoms. Here again, in the case of mixtures of any of a variety of different polycarboxylic acids, the number of carbon atoms refers to the average number within such a mixture.

Preference is given to using a dimerized or trimerized fatty acid which has preferably 30 to 60 carbon atoms, more preferably 36 to 54 carbon atoms. A dimer acid having on average 36 carbon atoms has proven very suitable. This dimer acid may also, preferably, include certain fractions of trimer acid or monoacid or tetramer acid.

Such polycarboxylic acids are available commercially under the trade names Empol (Cognis, Adhesives & Sealants) or Pripol (Unichema) or Versadyne (Henkel Hakusui Kabushiki Kaisha).

Examples of these products are as follows: Empol 1018, Empol 1045, Pripol 1013, Pripol 1006, Pripol 1022, Pripol 1009, Pripol 1010, Pripol 1040, Pripol 1010 or Versadyme 216.

According to one preferred development of the invention, the polyglycol ether comprises the group $R^1-X-(R^2-O)_y-(R^3-O)_z-(R^4-O)_k-$, where the $R^2-O$, $R^3-O$, and $R^4-O$ polyether units may be arranged randomly, alternately or as block copolymers.

The radical $R^1$ is a linear or branched aliphatic radical or araliphatic or aromatic organic radical having 1 to 30 carbon atoms.

The radicals $R^2$, $R^3$, and $R^4$ may be identical or, independently of one another, different, and are in each case a linear or branched aliphatic organic radical or araliphatic or aromatic organic radical having 1 to 12 carbon atoms.

The individual degrees of polymerization y, z, and k are natural numbers and are independently of one another 0 to 200, with the proviso that y+z+k=2 to 600.

The group X stands for O, S, (CO)O, or $NR^x$, where $R^x$ is H or an aliphatic radical having 1 to 20 carbon atoms. Preferably, X here is an oxygen atom or a carboxyl function, and more preferably an oxygen atom.

The polyglycol ether used for covalent linkage with the carboxylic acid is obtained preferably by reaction of an alcohol $R^1-OH$, a thiol $R^1-SH$, a carboxylic acid $R^1-COOH$ or an amine $R^1NHR$ as starter molecules with in each case an excess of glycols under suitable reaction conditions known to the skilled worker.

The polyglycol ethers of the invention are largely in the form of monofunctional polyglycols, since these polyglycols can be linked covalently to the carboxylic acids in an unambiguous way. By "largely monofunctional" here is meant that they have a fraction of 0% up to a maximum of 10% of difunctional polyglycol ether as well. In that case, either the radical $R^1$ contains a group which is reactive with the carboxylic acid, or, instead of the radical $R^1$, a hydrogen atom is present simply. The latter case, for example, is attributable to an incomplete reaction of the alcohols, thiols, etc. with the glycols.

The radical $R^1$ is preferably a linear or branched aliphatic radical or araliphatic or aromatic organic radical having 2 to 16 carbon atoms, and more preferably an aliphatic radical having 1 to 12 C atoms.

The radicals $R^2$, $R^3$, and $R^4$ have preferably, independently of one another, 2 to 8 C atoms, and more preferably 2 to 4 C atoms.

With particular preference the radicals $R^2$, $R^3$, and $R^4$ independently of one another are ethyl, isopropyl, propyl or butyl. Particular preference extends to alternating or blockcopolymer like ethyl, isopropyl units, so-called EO/PO polyethers.

The length of the ether units y+z+k is preferably 5 to 300, more preferably 7 to 100, and with particular preference 10 to 50.

Where ether units are too long, there is a decrease in the affinity of the additives for the metallic effect pigment surface. There is therefore a risk, in particular in a paste or a completed application medium, such as a printing ink, that the additive will detach from the metallic effect pigment or will not even bind sufficiently to the metallic effect pigment surface. If, on the other hand, the ether units are too short, then the additives, in terms of their effect on the properties of the metallic effect pigments, are no longer distinguishable or are barely distinguishable from the known lubricants.

Examples of suitable polyglycol ethers are methoxypolyethylene glycols, butoxypolyethylene glycols, methoxypolypropylene glycols or butoxypolypropylene glycols.

Prior to coupling to the carboxylic acid, the polyglycol ether or the polyglycol typically has a hydrogen atom or an amine function or an epoxide at the open end of the structural formulae shown above.

Accordingly, prior to the reaction with the carboxylic acid, the following molecules are preferred:

$R^1-X-(R^2-O)_y-(R^3-O)_z-(R^4-O)_k-H$ (formation of an ester)

$R^1-X-(R^2-O)_y-(R^3-O)_z-(R^4-O)_k-N(H)(R^5)R$ (formation of an amide)

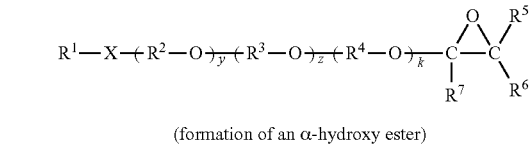

(formation of an α-hydroxy ester)

In the structural formulae above, $R^5$, $R^6$, and $R^7$ independently of one another are preferably H or a branched or unbranched carbon radical having 1 to 6 carbon atoms. The carbon radical is preferably a linear alkyl radical having 1 to 6 carbon atoms. The carbon radicals $R^5$, $R^6$, and $R^7$ may independently of one another be saturated or unsaturated. For example, $R^5$, $R^6$, and $R^7$ may independently of one another be phenyl radical. With particular preference $R^7$ and $R^8$ are an H and $R^6$ is an H or methyl.

Following reaction of the polyglycol ether with the carboxylic acid, there is preferably covalent coupling via the terminal oxygen atom.

According to one further variant, the carboxylic acid is partly or wholly esterified or amidated.

It has surprisingly been found that it is particularly advantageous if only some of the carboxyl groups are esterified, so that the carboxylic acid(s), preferably polycarboxylic acid(s), are present in the form of partial esters. Preferably at least 10% and not more than 90% of the carboxyl groups are esterified. With further preference about 15% to 80%, more preferably about 20% to 70%, of the carboxyl groups are esterified.

For coupling to the metallic effect pigment surface, therefore, preferably only a few carboxyl groups are needed in the additive.

It has emerged that the shelf life and also the mechanical properties, especially the splitting resistance, of a dried or cured application medium, such as a dried paint or printing ink or a cured varnish, for example, are improved if the carboxylic acids, preferably polycarbxylic acids, are present as partial esters.

In the case of this preferred variant, therefore, some of the carboxylic acids are still present in the form of carboxyl functions. It is thought that the additives having such carboxyl functions in the mixture according to the invention are able to bind particularly effectively to the metallic pigment surface.

The additives for use in accordance with the invention therefore preferably have acid numbers of 5 to 140, more preferably 6 to 100 mg KOH/g additive and very preferably of 8 to 50 KOH/g additive. These acid numbers are determined preferably in accordance with DIN 53402.

According to one further variant of the invention, the covalent coupling of carboxylic acid and polyglycol ether does not take place via an esterification or an amidation of the carboxyl functionalities of the carboxylic acid.

In this variant, for example, the additive is prepared from starting materials, on the one hand a carboxylic acid with hydroxyl functions (tartaric acid, for example) and on the other hand with a polyglycol ether which has a terminal epoxide group. In the carboxylic acid, the free carboxyl functions are relieved of their reactivity with the epoxide group by means of suitable protecting groups, and so the polyglycol ether is linked covalently by means of its epoxy function to the hydroxyl functions of the carboxylic acid, with formation of an α-hydroxyl ether bond.

According to one further variant of the invention, the carboxylic acid and the polyglycol ether can be coupled to one another via a hydrocarbon radical. This hydrocarbon radical may be saturated or unsaturated and comprises preferably 2 to 100 C Atoms. It is further preferred for the hydrocarbon radical to comprise 4 to 50, even more preferably 6 to 20, carbon atoms. With special preference the hydrocarbon radical preferably has a chain length in the range from 2 to 10 carbon atoms. The hydrocarbon radical may contain oxygen atoms and/or may be substituted. The hydrocarbon radical is preferably straight-chain, but may also be branched. In order to bring about covalent bonding of carboxylic acid and polyglycol ether, they are reacted with a difunctional reactive hydrocarbon. According to one preferred variant, diglycidyl compounds are used, preferably diglycidyl ethers.

In preferred embodiments, the additives possess a certain ratio of their hydrophilic polyether radicals to the hydrophobic hydrocarbon frameworks of the carboxylic acid or polycarboxylic acids. In this context, the ratio of the length of the polyether units y+z+k (degree of polymerization) to the number of carbon atoms in the polycarboxylic acid is preferably 0.1 to 4.0, more preferably 0.15 to 3.0, very preferably 0.2 to 2.0, and with particular preference 0.25 to 1.0.

Below a ratio of 0.1 it may be the case that the additives produce no inventive advantages in comparison to fatty acids. Above a ratio of 4.0 it may likewise be the case that no advantages can be observed any longer. In this case the additives tend no longer to be firmly attached to the metallic effect pigment surface.

According to one further variant, the carboxylic acids may also be partly esterified with monofunctional alcohols. The degree of esterification of the monofunctional alcohols is preferably 0% to 50% of the carboxylic acid functions present.

The monofunctional alcohols comprise a hydrocarbon radical having 1 to 20 C atoms. The hydrocarbon radical may be straight-chain or branched and saturated or unsaturated.

Examples of suitable alcohols are as follows: isopropanol, butanol, tert-butanol, amyl alcohol, isoamyl alcohol, n-hexanol, 2-ethylhexane, myristyl alcohol, n-octanol, isooctanol, isodecanol, caprylyl alcohol, lauryl alcohol, stearyl alcohol, tridecyl alcohol, hexadecyl alcohol, and mixtures of these alcohols.

The average molecular weight of the additive for use in accordance with the invention on the metallic effect pigments is preferably in a range from 200 to 20 000 g/mol, more preferably from 300 to 10 000 g/mol. An average molecular weight range from 500 to 8000 g/mol has proven very suitable, and a molecular range from 1000 to 4000 g/mol is particularly preferred.

According to one further variant of the invention, the carboxylic acid is present partly or wholly as carboxylic acid salt.

The carboxylic acid salts may comprise alkali metal cations and/or alkaline earth metal cations as cations. The cations of the carboxylic acid salts are preferably $Li^+$, $Na^+$, $K^+$, $Mg^{2+}$ and/or $Ca^{2+}$, and also mixtures of these.

The carboxylic acid salt is preferably a salt of the carboxylate of the carboxylic acid and one or more metal cations, the metal cations being selected preferably from the metals present in the metal core of the metallic effect pigment.

It has emerged as being advantageous, when using carboxylic acid salts, examples being metal soaps, to select those whose cation or cations match the metal or metals of the metallic effect pigment, so as not unnecessarily to introduce additional ions into an application medium.

According to one preferred variant, the metal cation or cations of the carboxylic acid salt are selected from the group of monovalent, divalent and/or trivalent metal cations.

Preferred cations are therefore $Al^{3+}$, $Fe^{3+}$, $Fe^{2+}$, $Cu^{2+}$ and/or $Zn^{2+}$.

These carboxylic acid metal salts may also be formed in situ from the carboxylic acids applied on the metallic pigments. The carboxylic acids may over time react with the metallic pigment to form the metal soap. This behavior is also known in respect of the fatty acids used on a standard basis as lubricants, such as stearic acid or oleic acid, for example.

According to one preferred embodiment, the additives are used as lubricants for the grinding of the metallic pigments. According to a further-preferred embodiment, no further additions of saturated or unsaturated fatty acids such as stearic or oleic acids are added to this lubricant. It has emerged that the advantageous effects of the lubricants of the invention tend to be impaired by the addition of conventional fatty acids during grinding.

According to a further embodiment, the additives are not added in the course of grinding, but instead only after grinding. Here, the effect of these additives derives in particular from the fact that it serves as an excellent dispersing assistant. The metallic pigment may in this case be incorporated outstandingly both into solvent borne and into aqueous application systems. The additives are added preferably to the metallic pigment filtercake or to a metallic effect pigment paste or powder.

In particular, metallic effect pigments treated in this way exhibit a significantly improved shelf life.

According to one advantageous development of the invention, the metallic effect pigments are present in compacted form, preferably as granules, pellets, tablets, briquettes, sausages or as paste.

The presentation forms referred to above allow low-dust handling, preferably dust-free handling, of the metallic effect pigments of the invention. The metallic effect pigments can easily be transported, metered, and processed without risk to humans or the environment.

In compacted form the metallic effect pigments preferably have a residual moisture content of up to about 15% by weight, more preferably of about 0.1% to about 10% by weight, more preferably still of about 0.2% to about 8% by weight, the % by weight figure being based on the total weight of the compacted metallic effect pigment preparation.

A method of the invention for producing the metallic effect pigments of the invention comprises the following steps:
a) grinding metal particles to metallic effect pigments in the presence of an additive which comprises at least one carboxylic acid having at least 4 carbon atoms, and also at least one polyglycol ether, the carboxylic acid and the polyglycol ether being bonded covalently to one another, and grinding media and also, optionally, a liquid phase,
b) separating the metallic effect pigments obtained in step a) and provided with the additive from the grinding media and optionally from the liquid phase,
c) optionally compacting the metallic effect pigments separated in step b) and provided with the additive.

All embodiments made above in relation to the metallic effect pigments of the invention and to the additive to be used apply correspondingly in the context of the method.

Metal particles used may be atomized metal powder, foil remnants or else metal platelets that have already been pre-shaped. The atomized metal powder may have an irregular form or a largely round form. In the case of the production of aluminum pigments or iron pigments, a largely round atomized metal powder form is preferred.

The deformation of the atomized metal powder may be carried out as a dry grinding or wet grinding process. The deformation of the atomized metal powder takes place preferably as a wet grinding process.

Solvents used may be organic solvents, solvent mixtures, such as of organic solvent and water, for example, or aqueous solvents. Where aqueous solvent is used it is preferred to add further corrosion inhibitors.

The wet grinding, however, takes place preferably in the presence of organic solvents. Organic solvents used are preferably solvent naphtha, naphtha, white spirit, esters, ethers, ketones, alcohols or glycols or mixtures thereof.

If it proves necessary, the metallic effect pigments may typically be rewetted after grinding. This means that, under reduced pressure and at elevated temperatures, they are largely freed from their solvent and are then pasted up again with the solvent compatible (and desired by the customer) for the particular end application.

Where very thin metallic effect pigments (average thickness <100 nm and especially ≤50 nm) are produced, however, the rewetting step, on account of the very high specific surface areas of the pigments, may be accompanied by unwanted instances of agglomeration of the metallic pigments. In this case, grinding ought preferably to be carried out in solvents which are compatible with the subsequently planned application.

For application in a gravure printing ink, for example, solvents such as ethyl acetate, n-propyl acetate or isopropyl acetate are preferred.

According to one preferred variant, step a) is carried out in a ball mill in the presence of grinding media, preferably of spherical grinding media.

Spherical grinding media, preferably balls, that are used are preferably glass balls, steel balls and/or ceramic balls. Ceramic balls used are preferably balls of corundum or zirconium oxide.

The average ball diameter is preferably 0.3 up to 5.0 mm, more preferably 0.5 to 4.5 mm, and very preferably 0.6 to 2 mm.

The grinding media used for the wet grinding of atomized copper or brass powder preferably have an individual weight of 85 µg to 515 mg.

According to one preferred development of the invention, the grinding media have an individual weight of 0.8 to 180 mg.

In the case of steel balls, the average individual weight is preferably in a range from 1 to 180 mg, preferably of 1.2 to 150 mg, more preferably of 2.0 to 120 mg. In the case of glass balls, the average individual weight is in a range from 1.0 to 12.5 mg.

During the deformative grinding, the temperature is preferably in a range from 10° C. to 70° C., more preferably from 25° C. to 45° C. The grinding time in this case is preferably in a range from 2 to 120 h, preferably from 5 to 100 h, more preferably still from 8 to 80 h.

For the preferred case of the production of very thin metallic effect pigments (<100 nm average thickness) it is necessary to estimate very long grinding times. In this case the pigments must be cautiously shaped. Preferred grinding times for metallic effect pigments are at least 15 h, more preferably at least 20 h. These times should be understood to be total grinding duration times.

If grinding is carried out in two or more different steps, then the grinding times of the individual steps are to be added up accordingly.

In a further preferred method of the invention, the additive is not used as a lubricant for the grinding of the metallic pigments. The method in this case comprises the following steps:
a) grinding an atomized metal powder or metal foil scraps in the presence of grinding media and optionally solvent with a lubricant to give platelet-shaped metallic effect pigments, b) separating the platelet-shaped metallic effect pigments from the grinding media and optionally from the major part of the solvent, c) adding and combining the additive for use in accordance with the invention to the metallic pigment powder or optionally filtercake from step b).

The choice of the solvents or of the grinding media (grinding balls) in this case is the same as described above.

Inventive mixtures of this kind of metallic effect pigment and additive are notable for particularly effective dispersing of the metallic effect pigments in an application medium. As a result of the treatment with additive, the metallic effect pigments are largely not agglomerated. The metallic effect pigments are notable for a very long shelf life and easy processing in application media such as printing inks or paints. For instance, in particular, the dispersion step typical when using metallic effect pigments in paints, in which the metallic effect pigment is predispersed together with solvent (generally butylglycol) and optionally wetting agents, can largely be dispensed with or can be implemented very well without wetting agents. The metallic effect pigment can be dispersed outstandingly simply by means of the additive, which acts as a dispersant.

The amount of additive used in this context is dependent on the end use and especially on the specific surface area of the metallic effect pigment.

It is further preferred for the compacting to be carried out by means of granulating, palletizing, tableting, briquetting, filtering, pressing and/or extruding.

Granulation can be accomplished, for example, by spray granulation. For pelletizing it is preferred to use pelletizing plates. Tableting and briquetting is carried out preferably by compression molding into corresponding shapes. The sausage shape is produced preferably by extruding the metallic effect pigments.

The metallic effect pigment of the invention with additive, of any of claims 1 to 12, is used preferably for producing coating compositions, especially paints, coatings, printing inks, plastics or cosmetic formulations.

The present invention accordingly also provides a coating composition, such as paints, coatings, printing inks, plastics or cosmetic formulations, for example, which comprises the metallic effect pigment of the invention with additive, of any of claims 1 to 12.

In one preferred embodiment the present invention provides a printing ink which comprises an inventive mixture of additive and metallic effect pigment. It is particularly preferred in this case to use the additive as a lubricant when producing the metallic effect pigment by grinding, preferably by wet grinding.

The printing ink is preferably a liquid printing ink such as a gravure, flexographic or screen printing ink. It may of course also be an offset printing ink or a digital printing ink.

In the case of digital printing ink, inkjet printing inks are particularly preferred. In this case only very fine metallic effect pigments may be used. These fine metallic effect pigments have an average size $d_{50}$ of 0.65 to 10 μm, preferably of 0.7 to 8 μm and more preferably of 0.8 to 6 μm. Such fine metallic effect pigments are necessary here since otherwise there is clogging of the feed lines and/or injection nozzles.

The gravure, flexographic or screen printing inks of the invention comprise solvents or solvent mixtures. These are used, among other things, to dissolve the binders, but also to set important application properties of the printing inks, such as the viscosity or the drying rate, for example.

Solvents used for liquid printing inks such as flexographic and gravure inks comprise, in particular, low-boiling solvents. The boiling point is generally not more than 140° C. Higher-boiling solvents are used only in relatively small amounts, to set the drying rate. The formulation of screen printing inks is similar to that of flexographic or gravure inks, but just with a slightly higher viscosity and usually with solvents having somewhat higher boiling points. Examples of suitable solvents for liquid printing inks include ethanol, 1-propanol or 2-propanol, substituted alcohols such as, for example, ethoxypropanol or esters such as, for example, ethyl acetate, isopropyl acetate, n-propyl acetate or n-butyl acetate. It is of course also possible to use mixtures of different solvents. For example, the solvent may comprise a mixture of ethanol and esters such as ethyl acetate or propyl acetate. For printing with flexographic printing plates it is generally advisable for the fraction of the esters as a proportion of the total solvent not to exceed about 20%-25% by weight. As the solvents for liquid printing inks it is also possible with preference to use water or predominantly aqueous solvent mixtures.

Depending on the type of printing ink it is usual to use 10% to 60% by weight of solvent, relative to the sum of all the ingredients. In the case of the printing inks of the invention, however, a range of 60%-80% by weight of solvent is found to be particularly advantageous.

Radiation-curable printing inks generally do not contain the abovementioned solvents, but instead contain reactive diluents. Reactive diluents typically fulfill a dual function. First, they act to crosslink or cure the printing ink, and second, however, they also act like conventional solvents (DE 20 2004 005 921 UI 2004.07.1) to adjust the viscosity. Examples include butyl acrylate, 2-ethyl-hexyl acrylate, and also, in particular, polyfunctional acrylates such as 1,4-butanediol di(meth)acrylate, 1,6-hexanediol di(meth)acrylate or trimethylolpropane tri(meth)acrylate.

As binders for the metallic printing inks of the invention it is possible in principle to use the binders that are typical of liquid printing inks. Depending on the desired end application and on the desired properties, the skilled worker makes an appropriate selection. Examples of suitable binders include polyesters, polyamides, PVC copolymers, aliphatic and aromatic ketone resins, melamine-urea resins, melamine-formaldehyde resins, maleinates, rosin derivatives, casein and casein derivatives, ethylcellulose, nitrocellulose or aromatic and/or aliphatic polyurethanes. Use may also be made of polymers or copolymers of vinyl acetate, vinyl alcohol, acrylates, methacrylates, vinylpyrrolidone or vinyl acetals. With particular advantage it is possible to use hyperbranched polymers containing functional groups, examples being hyperbranched polyurethanes, polyureas or polyesteramides, as disclosed in WO 02/36695 and WO 02/36697. It is of course also possible to use mixtures of different polymeric binders, subject to the proviso that the selected binders do not have unwanted properties in combination with one another. The amount of all binders is typically 5%-40% by weight, based on the sum of all the ingredients of the printing ink.

Particularly preferred binders include, for example, nitrocellulose, ethylcellulose, hydroxyethylcellulose, acrylates, polyvinyl butyrals, and aliphatic and aromatic polyurethanes and polyureas, especially hyperbranched polyurethanes and polyureas and mixtures thereof.

Binders contemplated for water-reducible metallic printing inks include, in particular, copolymers based on (meth)acrylic acid and/or esters thereof with styrene. Binders of this kind are available commercially as solutions or dispersions for use in printing inks, under the name Zinpol® (Worlee), for example. Further examples include aromatic and/or aliphatic aqueous polyurethanes, polyesters, and aqueous polyamides.

For pastelike printing inks, preferred binders include, for example, rosins or modified rosins. Examples of modified rosins include rosins esterified wholly or partly with polyols such as glycerol or pentaerythritol, for example.

Radiation-curable printing inks comprise binders which comprise crosslinkable groups, such as olefinic groups, vinyl ether groups or epoxide groups, for example. Here, the sum of the binders (including reactive diluents) is generally in a range of 30%-90% by weight of all the ingredients of the printing ink.

The metallic printing inks of the invention may further comprise one or more auxiliaries or additives. Examples of additives and auxiliaries are fillers such as calcium carbonate, aluminum oxide hydrate or aluminum or magnesium silicate. Waxes increase the abrasion resistance and serve to increase the lubricity. Examples are, in particular, polyethylene waxes, oxidized polyethylene waxes, petroleum waxes or ceresin waxes. Fatty acid amides can be used to increase the surface smoothness. Plasticizers serve to increase the elasticity of the dried film. For radiation-curable printing inks at least one photoinitiator or a photoinitator system is used additionally as additive. For dispersing the effect pigments it is possible to use dispersing assistants. Floating of the metallic effect pigments in the printed layer can be achieved by means of fatty acids, with the pigments accumulated in/at the upper interface of the printed layer. By this means it is possible with advantage to achieve improved metallic effects. Furthermore, antisettling agents may be added as well. Additions of this kind prevent sedimentation of the effect pigments. Examples include silica, cellulose derivatives or else waxes. With the metallic effect pigments of the invention, however, it is possible, advantageously, not to use settling agents, or to reduce the fraction of settling agents.

For the formulation of the particularly preferred low-viscosity flexographic, gravure or screen printing inks, the addition of antisettling agents is usually advisable, although not always absolutely necessary. The total amount of all additives and auxiliaries ought typically not to exceed 20% by weight, based on the sum of all the ingredients of the printing ink, and is preferably 0.1%-10% by weight.

The metallic printing inks of the invention can be produced in a way which is known in principle, by intense mixing and dispersing of the ingredients in typical apparatus such as dissolvers or agitators, for example. When using dissolvers, the skilled worker will ensure that the energy input is not too high, so as to prevent damage to the metallic effect pigments of the invention. On the other hand, it must of course be high enough to allow proper dispersing of the pigments. If customary color pigments are used in addition to the metallic effect pigments of the invention, it may be advisable to predisperse them in a portion or the entirety of the solvent, binder, and, where appropriate, auxiliaries of the metallic printing ink, and to add the metallic effect pigments of the invention only later. In this way, particularly effective dispersing of the additional pigments is achieved, without the metallic effect pigments suffering damage from excessive dispersing. Instead of the pigments it is also possible to add predispersed pigment concentrates. In this case, in an especially elegant way, it is also possible to use a commercially customary printing ink in small amounts, provided the added printing ink is compatible with the formula of the metallic printing ink and does not impair its properties.

EXAMPLES

The examples which follow illustrate the invention, but without restricting it.

A Aluminum Effect Pigment Examples

Example 1a 50 g of Pripol 1009 (hydrogenated C36 dimer acid from Unicherna) and 89 g of MPEG 750 (methoxypolyethylene glycol) were weighed out into a glass reaction vessel and heated to 80° C. with stirring under $N_2$ inert gas. Then 0.8 g of p-toluenesulfonic acid (catalyst) was added and heating took place to 180° C. Water of reaction formed was separated off using a water separator. The progress of reaction was monitored on the basis of the acid number. The acid number was determined in accordance with DIN 53402. The reaction was halted when an acid number of around 24 mg KOH/g additive was reached. This corresponds to a degree of esterification of approximately 67%. The average molecular weight of the resulting ester was approximately 1750 g/mol, the ratio of the ether units to C atoms being approximately 0.3.

Example 1b 100 g of atomized aluminum powder having the grain-size distribution parameters (average particle size $d_{50, powder}$=2.2 μm, $d_{10, powder}$ 1.1 μm, $d_{90, powder}$ 3.6 μm) and 440 g of isopropyl acetate, and also 8 g of the additive from example 1a, were placed in a pot mill (length: 32 cm, width: 19 cm) and the mill was closed. Grinding then took place at 50 rpm for 12 h using 4.5 kg of steel balls (diameter: 1.8 mm). Grinding then took place in a second milling stage at 24 rpm for 13 h. The grinding product discharged from the mill was washed with isopropyl acetate and separated from the grinding balls by means of a screening (24 μm). The screened material was largely freed from isopropyl acetate by means of a suction filter, and then pasted up again with isopropyl acetate in a laboratory mixer (approximately 65% by weight solids fraction).

Example 2

Grinding formula as example 1b, but using, as lubricant, 8 g of the commercially available fatty acid polyglycol ester P 4100 (Byk, Wesel, Germany).

Example 3

Grinding formula as in example 1b, but using an atomized aluminum powder having an average particle size $d_{50, powder}$=1.7 μm, $d_{10, powder}$ 0.4 μm, $d_{90, powder}$ 2.3 μm.

Example 4

Grinding as in example 3, but using, as lubricant, 8 g of the commercially available dispersing additive P 4100 (Byk, Wesel, Germany).

Comparative Example 5

Grinding as in example 1b, but using, as lubricant, 3 g of a customary mixture of stearic and oleic acid.

Comparative Example 6

Grinding as in example 3, but using, as lubricant, 3 g of a customary mixture of stearic and oleic acid.

Comparative Example 7

Commercially available aluminum pigment (platinum dollar pigment) Platinvario 85001 (Eckart, Germany).
In this case use was made as lubricant of a customary mixture of stearic and oleic acid.

Comparative Example 8

VP 55000

Commercially available non-leafing silver dollar pigment VP 55000 (Eckart, Germany).
In this case use was made as lubricant of a customary mixture of stearic and oleic acid.
Customary laser diffraction methods (instrument: Cilas 1064, Cilas, France) were used to ascertain the size distribution of the aluminum effect pigments. By means of the method described in WO 2004/087816 A2, the average thickness $h_{50}$ was determined on the basis of SEM counts. The results of this pigment characterization are shown in table 1.

TABLE 1

Physical characterization of the pigments

| Sample | Lubricant | Particle size distribution | | | Average thickness (SEM) |
|---|---|---|---|---|---|
| | | $d_{10}/\mu m$ | $d_{50}/\mu m$ | $d_{90}/\mu m$ | $h_{50}/nm$ |
| Example 1b | Example 1a | 4.3 | 9.4 | 15.1 | about 50 |
| Example 2 | P 4100 | 4.1 | 9.2 | 14.7 | |
| Example 3 | Example 1a | 4.8 | 11.1 | 18.7 | about 50 |
| Example 4 | P 4100 | 4.4 | 10.6 | 18.3 | |
| Comparative example 5 | Stearic/oleic acid mixture | 4.3 | 9.1 | 14.6 | about 55 |
| Comparative example 6 | Stearic/oleic acid mixture | 4 | 9.7 | 17.1 | about 65 |
| Comparative example 7 | Stearic/oleic acid mixture | 5.8 | 10.2 | 15.6 | 60 |
| Comparative example 8 | Stearic/oleic acid mixture | 4.7 | 9.1 | 14.6 | — |

Results of Optical Assessment:

The pigments of the inventive examples and of the comparative examples were assayed in the following test systems for coatings (NC varnish) and prints.
The following systems were used here:
a) Gravure printing ink based on commercially available nitrocellulose H 33, with a level of pigmentation of 11.0% by weight and an ethanol/ethyl acetate solvent mixture.
b) Gravure printing ink based on commercially available acrylate binders, with a level of pigmentation of 10.8% by weight and an ethanol/ethyl acetate solvent mixture.
c) Reverse-face applications (mirror varnish) based on a commercial available polyvinyl butyral binder, with a level of pigmentation of 9.8% by weight and an ethanol/ethyl acetate solvent mixture.
The reverse-face applications in tab. 2 were produced using a gravure printing ink based on a commercially available polyvinyl butyral, by printing on a MELINEX 400 film (PET film, 50 μm), using an applicator having a groove depth of 24 μm.
d) NC varnish drawdowns: the commercially available nitrocellulose (NC) varnish Dr. Renger Erco Bronzemischlack 2615e (Morton) was used, with a level of pigmentation of 7.1% and an applicator depth of 24 μm.

Gloss:

The gloss values were obtained in each case using the Micro-Tri-Gloss instrument (Byk-Gardner, Geretsried, Germany) at a measuring angle of 60. The instrument here was calibrated by means of dark calibration and also with a black mirror glass plate having values of 95.5 for 60°.

Splitting Resistance:

To test the splitting resistance between pigment and binder in the inventive and comparative examples, drawdowns were produced from the above-mentioned varnishes and inks. Following complete curing of the ink or paint coat, an adhesive strip was adhered to the surface of the drawdowns, firmly and without bubbles. This adhesive strip was then peeled off again, and so the substrate (e.g., paper) was not damaged. The splitting resistance was assessed visually on the basis of a rating system. A poor splitting resistance is reflected in a correspondingly severe extraction from the print or coating.

Hiding/Transfer Behavior:

The hiding or transfer behavior of the inventive and comparative examples was determined by means of prints. Transfer behavior refers to the transfer of metal pigment from the printing plate (or printing cells) to the printed article. The transfer behavior was assessed visually on the basis of a rating system. Prints with poor transfer behavior are unacceptable from a performance standpoint. A poor transfer behavior also, of course, has the effect of a poor hiding behavior, since there is less pigment present in the application.

Rating 0: very good
Rating 1: good
Rating 2: satisfactory
Rating 3: adequate
Rating 4: poor
Rating 5: very poor It was found that the gloss values are critically dependent in each case on the varnish or printing ink systems used. The interlayer adhesion also varies as a function of the binder. Generally speaking, however, in the case of the applications with the pigments of the invention, it is possible to observe good to very good splitting resistance in conjunction with relatively high gloss and a satisfactory to very good hiding/transfer behavior.

The inventive examples perform much better in the combination of these properties than do the comparative examples.

In detail, in comparative example 7, very high gloss values can also be observed in the gravure printing inks. This pigment, however, shows poor splitting resistance and a poor hiding/transfer behavior.

The pigment size distribution of comparative example 6 is very similar to that of example 1b. In the case of the gravure printing applications, however, the gloss is lower and in some cases the transfer behavior is poor. In the mirror application, a very high gloss is achieved, but the splitting resistance is not so good.

In the nitrocellulose varnish application, in comparison to comparative examples 5 and 6, there is no deterioration in the gloss value, and in fact an increase by 30% can be achieved.

TAB 2

Results of assessments, aluminum pigments

| Sample | Gravure printing ink testing a) nitrocellulose | | | Gravure printing ink testing b) acrylate | | | c) Mirror varnish application | | NC varnish | |
|---|---|---|---|---|---|---|---|---|---|---|
| | Gloss (60°) | Splitting resistance | Hiding/ transfer | Gloss (60°) | Splitting resistance | Hiding/ transfer | Gloss (60°) | Splitting resistance | Gloss (60°): | Splitting resistance: |
| Example 1b | 127 | good (1) | very good (1) | 80.3 | very good (0) | good (2) | 495 | very good (0) | 123 | very good (0) |
| Example 2 | 120 | very good (0) | very good (0) | 75.4 | very good (0) | not very good (3) | 494 | poor (4) | 91.7 | very good (0) |
| Example 3 | 137 | good (1) | good (1) | 78.5 | very good (0) | good (2) | 465 | not very good (3) | 106 | very good (0) |
| Example 4 | 119 | very good (0) | very good (0) | 79.8 | very good (0) | good (2) | 507 | good (1) | 98.9 | very good (0) |
| Comparative example 5 | 101 | not very good (3) | good (2) | 70.0 | very good (0) | good (2) | 466 | good (2) | 61.7 | very good (0) |
| Comparative example 6 | 116 | good (2) | poor (3) | 75.6 | very good (0) | good (2) | 522 | not very good (3) | 109 | good (0) |
| Comparative example 7 | 122 | poor (5) | poor (4) | 82.5 | poor (4) | poor (4) | 605 | poor (4) | 131 | poor (5) |
| Comparative example 8 | 88.7 | poor (4) | poor (3) | 69.2 | not very good (3) | poor (4) | 357 | poor (4) | 60.5 | poor (4) |

Examples of Inventive Metallic Effect Pigments with Additive, and Comparative Examples:

In addition to the improvement in the performance properties of aluminum effect pigments through use of the additives as lubricants during grinding, the additive may also be used for the subsequent stabilization of pigment filtercakes.

Comparative Example 9

Commercially available silver dollar pigment MEX 2192 (Eckart).
This pigment is ground with a mixture of stearic and oleic acid.

Example 10

Commercially available silver dollar pigment MEX 2192, after grinding, is combined in the filtercake with 2% by weight of additive from example 1a, homogenized in a mixer, and then processed further to give a metallic effect pigment paste.

As is known, metallic pigment pastes have a tendency on prolonged storage to form agglomerates, which can no longer be broken down even by relatively intensive dispersion. As a generally recognized test for this behavior, samples are stored in sealed press-on-lid containers at 50° C. and examined at regular intervals for agglomerates (applicator drawdowns on contrast card). The increased temperatures simulate a significantly longer storage time under standard conditions.

TABLE 3

Results of storage at 50° C. in days:

| Sample | Shelf life duration |
|---|---|
| Comparative example 9 (Mex 2192) | 28 d |
| Example 10 | >140 d |

In order to investigate the parameters of hiding and gloss, which are relevant for printing application, the metallic effect pigment of the invention, after the storage described above, was applied to film in a gravure printing ink based on commercially available nitrobinder (LQ 2903). The gloss values and the hiding were determined in the manner described above.

Example 11

Commercially available silver dollar pigment IL Reflexal VP-62617/G (Eckart), after grinding, is combined in the filtercake with 2% by weight of an additive from example 1a, and then processed further to give a metallic effect pigment paste.

Comparative Example 12

Commercially available silver dollar pigment IL Reflexal VP-62617/G (Eckart).

Example 13

Commercially available silver dollar pigment AF Reflexal VP-58187/G, after grinding, is combined in the filtercake with 2% by weight of an additive from example 1a, and then processed further to give a metallic effect pigment paste.

Comparative Example 14

Commercially available silver dollar pigment AF Reflexal VP-58187/G (Eckart)

TABLE 4

Results of visual assessment after 6 weeks of storage at 50° C.

| Sample | Hiding | | Gloss | |
|---|---|---|---|---|
| | fresh | after 6 weeks | fresh | after 6 weeks |
| Example 11 | moderate (3) | moderate (3) | 255 | 223 |
| Comparative example 12 | moderate (3) | relatively low (1) | 247 | 200 |
| Example 13 | moderate (3) | moderate (3) | 154 | 155 |
| Comparative example 14 | moderate (3) | moderate (3) | 150 | 141 |

The metallic effect pigments of example 11, after storage, have comparatively equal hiding and somewhat lower gloss in the application. The metallic effect pigments of comparative example 12 likewise feature a reduction in gloss. The gloss, however, is generally lower than in the case of example 1. In contrast, the opacity decreases in the case of comparative example 12, suggesting incipient agglomeration.

The metallic effect pigments of example 13 feature virtually no changes at all in terms of hiding and gloss after storage. The metallic effect pigments of comparative example 14, in contrast, do show no change in hiding behavior, but exhibit a marked detraction in gloss.

B GOLD-BRONZE EFFECT PIGMENT EXAMPLES

Example 15 a) Metal Powder Atomization

Brass pigments of the invention were produced by charging an induction furnace with 70% by weight of copper and 30% by weight of zinc, and melting this initial charge. The brass melt was then transferred to a channel-type induction furnace with forehearth. The brass melt present in liquid form at a temperature of around 1050° C. in the forehearth was atomized vertically downward by means of an atomizing nozzle mounted in the forehearth. The nozzle used for atomizing the brass melt was a close-coupled nozzle. The brass particles formed in the course of atomization solidify and cool while in flight. Atomization took place with supply of hot air at around 400° C. The hot gas used for atomizing was compressed, then heated in gas heaters, and subsequently introduced into the brass melt to be atomized. The brass particles were deposited by means of centrifugal force. The atomized brass powder deposited had a $d_{50}$ of <60 μm. Gas/solids separation took place in a filter. Further separation of this atomized brass powder took place in additional classifying steps. The result was an ultrafine atomized brass powder ("brass 70:30 rich gold"), produced with a $d_{10}$ of 1.4 μm, a $d_{50}$ of 2.4 μm, and a $d_{90}$ of 4.0 μm, and also a $d_{98}$ of 6 μm.

b) Grinding

For the wet grinding of the ultrafine atomized brass powder produced in step a), 400 g of this atomized metal powder were introduced into a mill (length: 32 cm, width: 19 cm) with 10 kg of chrome steel balls (diameter: 3 mm) and 900 g of isopropyl acetate and also 30 g of grinding additive from example 1b, and grinding took place at 80 rpm for 30 h. The ground product was separated from the grinding balls by rinsing with solvent, and isolated by filtration. The filtercake was then introduced into a second mill. The brass paste introduced into this mill, with a quantity of 400 g, was ground using 10 kg of chrome steel balls (diameter: 1.3 mm) with a rotational speed of 60 rpm for 30 h with approximately 900 g of isopropyl acetate and about 25 g of grinding additive from example 1b. The brass pigment paste was then separated from the grinding balls by rinsing with solvent, and thereafter concentrated to a solids content of 70% by weight.

Example 16

The same as example 15, but carrying out grinding using N-propyl acetate as solvent instead of isopropyl acetate.

Comparative Example 17

Commercially available gold-bronze pigment powder for gravure and flexographic printing inks ("Rotoflex" from Eckart GmbH) is produced by the known multistage dry grinding process (Hametag process) using stearic acid as grinding assistant. The starting material used was an atomized brass powder with 70% by weight copper and 30% by weight zinc, having an average particle diameter $d_{50}$ of 140 μm. The leafing gold-bronze pigments present as classified ground material, having an average particle diameter $d_{50}$=8 μm, were used to produce a gold-bronze pigment having non-leafing properties, by means of subsequent surface modification with 2.5% by weight of citric acid.

Comparative Example 18

Commercially available PVD pigment Metalure A (Eckart GmbH, Germany).

This pigment is present in the commercially available printing ink ("ULTRASTAR", Eckart) for gravure and flexographic printing.

This printing ink further comprises a yellow and an orange toner dye, in order to evoke a gold color.

To determine the particle thicknesses, samples of example 15 to 18 were characterized by means of a field ion scanning electron microscopy.

For determining the thickness distribution by means of SEM, the samples were prepared as follows:

The plated-shaped brass pigments produced from wet-ground atomized brass powder, and present in the form of a paste or filtercake, are washed with acetone and subsequently dried.

A resin customary in electron microscopy, an example being TEMPFIX (Gerhard Neubauer Chemikalien, D-48031 Münster, Germany), is applied to a sample plate and heated on a hotplate until it softens. The sample plate is then removed from the hotplate and the brass powder is scattered over the softened resin. As a result of cooling, the resin resolidifies and the scattered brass pigments can be prepared in such a way that they are fixed on the sample plate standing almost vertically, by virtue of the interaction between adhesion and gravity. As a result, the brass pigments can be measured well from the side in the electron microscope. In the measurement of the thickness, the azimuthal angle of the pigment to a plane normal to the surface is estimated, and is taken into account for the thickness evaluation in accordance with the formula $$h_{eff}=h_{meas}/\cos\alpha,$$

The cumulative distribution curve is plotted from the calculated $h_{eff}$ values by means of the relative frequencies. 50 to 100 particles are counted in each case.

Tab. 5 below shows the physical characteristics of the inventive brass pigments (example 15) in comparison to commercially traded gold-bronze pigment powder (comparative example 17) from Eckart and to the PVD aluminum pigment (comparative example 18) from Eckart, on the basis of the $d_{10}$, $d_{50}$ and $d_{90}$ values, and the characteristic values $h_{10}$, $h_{50}$ and $h_{90}$, and span values of the thickness measurement that are calculated from them, from the REM investigations. The $h_{10}$, $h_{50}$, and $h_{90}$ values were calculated by means of the quantile function from the original thickness count data.

The longitudinal extent d of the pigments was determined by means of a laser granulometer (Cilas 1064, Cilas, France) and the measure selected for the average longitudinal extent was, as usual, the $d_{50}$ value of the cumulative undersize distribution in μm.

TABLE 5

Physical characterization, gold-bronze pigments

| | Sizes | | | Thicknesses | | | Span of thickness distribution [%] | Form factor |
|---|---|---|---|---|---|---|---|---|
| Samples | $d_{10}$ [µm] | $d_{50}$ [µm] | $d_{90}$ [µm] | $h_{10}$ [nm] | $h_{50}$ [nm] | $h_{90}$ [nm] | | |
| Example 15 | 3.5 | 8.3 | 13 | 20.2 | 26.2 | 35.8 | 0.6 | 317 |
| Example 16 | 2.9 | 8.2 | 12.6 | 13.6 | 18.3 | 25.8 | 0.67 | 448 |
| Comparative example 17 | 3.3 | 8 | 15 | 29.9 | 45.2 | 74.1 | 1 | 177 |
| Comparative example 18 | 3.5 | 10 | 17.5 | 21 | 29 | 38.7 | 0.6 | 476 |

The figures in tab. 5 show that the inventive non-leafing brass pigments of examples 15 and 16 have not only a lower average thickness $h_{50}$ but also a lower $h_{90}$ value than the "ROTOFLEX" stabilized leafing gold-bronze pigments, from Eckart GmbH, D-90763 Fürth, of comparative example 17. Surprisingly, they even have lower pigment thicknesses than the "Metalure A" PVD aluminum pigments from Eckart, from comparative example 18.

The span of the thickness distribution is comparable in the case of the inventive pigments with the PVD aluminum pigments. This was hitherto unobtainable from wet grinding. The conventional gold-bronze pigment from wet grinding (comparative example 17) shows a significantly higher span.

It is also evident from tab. 5 that the inventive brass pigments of example 15 have a substantially narrower thickness distribution (span) than the conventional gold-bronze pigments of comparative example 17. Moreover, the inventive brass pigments of examples 15 and 16 have a lower parameter $d_{90}$ than the pigments of comparative examples 17 and 18.

For further characterization of the inventive brass pigments, so-called reverse applications were made on transparent films. This was done by printing a MELINEX 400 film (PET film, 50 µm) with a gravure ink based on a commercially traded polyvinyl butyral (PVB) and on a mixture of methoxypropanol and ethyl acetate, using a printing machine.

The pigmented reverse film applications were characterized optically by gloss measurement at 60° in accordance with DIN 67 530 (instrument: micro-TRI-gloss from Byk-Gardner, D-82538 Geretsried, Germany). Calibration took place by means of dark calibration and also a black mirror glass plate with values of 92 for 60°.

The color density was measured using a densitometer (instrument: densitometer, X-Rite, D-63263 Neu-Isenburg). Calibration took place using a white standard and the unprinted substrate at a wavelength in the yellow region.

Color density=−1g reflectance

Measurement takes place of the surfaces viewed straight on.

The optical properties, determined on the basis of printing-machine prints (printing machine: Rotova 300, Rotocolor, 3 ink units; printing speed 75 m/min, viscosity 15 s DIN 4 flow cup, 60, 70, 80 and 90 lines/cm; level of pigmentation 25%), of reverse film applications pigmented with inventive brass pigments from example 15 and conventional gold-bronze pigments from comparative example 17, and also with colored, conventional PVD aluminum pigments from comparative example 18, are shown in tab. 6 below.

In the case of comparative example 18, the printing ink ULTRASTAR (Eckart) with two different concentrations of a mixture of yellow (Yellow 79) and orange (Solvent Orange 41) dyes was used (example 18a and 18b). The dyes were mixed in the form of the UltraStar toner series (UltraStar Toner TY-21 and TO-11; Eckart), the toner series comprising in each case dispersions of the dyes in methoxypropanol.

TABLE 6

Optical characterization, pigments I

| | Gloss (60°) | | | | Color density | | | |
|---|---|---|---|---|---|---|---|---|
| | Lines/cm | | | | | | | |
| Sample | 60 l/cm | 70 l/cm | 80 l/cm | 90 l/cm | 60 l/cm | 70 l/cm | 80 l/cm | 90 l/cm |
| Example 15 | 500 | 488 | 440 | 428 | 1.45 | 1.44 | 1.32 | 1.22 |
| Comparative example 17 | 243 | 246 | 232 | 230 | 1.00 | 1.00 | 0.84 | 0.77 |
| Comparative example 18a (colored with 35% toner) | 415 | 408 | 405 | 396 | 1.50 | 1.52 | 1.50 | 1.44 |
| Comparative example 18b (colored with 59% toner) | 210 | 207 | 208 | 209 | 1.48 | 1.86 | 1.94 | 1.80 |

Tab. 6 shows that reverse film applications comprising inventive brass pigments from example 15 have a greater gloss, for all of the printing variants, than the reverse film applications pigmented with conventional pigments from comparative examples 17 and 18.

Relative to comparative example 17, moreover, the applications of the inventive pigments from example 15 have a higher color density.

The gloss of the reverse film applications of example 15 was likewise higher than for comparative examples 18a and 18b. The higher color densities of comparative examples 18a and 18b, however, suggest a greater coloredness of these applications than for example 15. In actual fact, however, this was not the case.

Indeed, visual assessment of the mirror effect of the reverse film applications gave the following results:
Example 1: clear, very good mirror
Example 4: mirror matt, hazy
Example 5a: weakly colored, silvery mirror
Example 5b: matt mirror For further optical characterization, the lightnesses, the chroma, and the hue angle of the pigmented reverse film applications were determined, with the experimental results recorded in tab. 7 below. Lightness measurements were carried out using a commercially available instrument from X-Rite (light source D65, 10° standard observer) in diffuse measurement geometry, with an observation angle of 8°. In this case, as an example, the values at 60 1/cm were measured.

The chroma C* recorded in tab. 7 describes the relative saturation in relation to the reference white, in other words in comparison to a defined lightest point in a color space. The hue angle h*, which is likewise recorded in tab. 7, is the color value assigned to the color shade, which is also identified as hue.

TABLE 7

Optical characterization of gold-bronze pigments
II, diffuse measuring geometry

| Sample | L* | a* | b* | c* | H* | Gloss (60°) 60 1/cm |
|---|---|---|---|---|---|---|
| Example 15 | 84.5 | 3.0 | 31.5 | 31.6 | 84.5 | 500 |
| Comparative example 17 | 78.8 | 3.6 | 27.9 | 28.2 | 82.7 | 243 |
| Comparative example 18a (colored with 35% toner) | 83.8 | 0.0 | 10.2 | 10.2 | 89.8 | 415 |
| Comparative example 18b (colored with 59% toner) | 77.2 | 0.2 | 27.4 | 27.4 | 89.5 | 210 |

From tab. 7 it is apparent that the inventive brass pigments from example 15 were more intensely colored than those of comparative examples 17 and 18a and 18b. These measurements also corresponded much more to the visual impression. This means that the gold-bronze pigment from example 15, on account of its low pigment thickness, possessed a high gloss and also, owing to its inherent color, a high color value (chroma). It is also evident from tab. 7 that the optical properties of the toner-colored reverse film applications from examples 18a and 18b correlated with the amount of toner used as colorant. Hence the reverse film applications from example 18b, that contained more colorant (toner), did give a higher chroma (C*), but gave lower lightnesses L* and a substantially reduced gloss (60°) than the reverse film applications of example 18a, containing a lower level of dyes (toner). Evidently, the dyes scatter the light too much and so reduce the metallic effect. These disadvantages can be overcome with the inventive metallic effect pigments.

As a further criterion for assessment, the adhesive strength of the pigmented reverse applications was determined by means of an adhesive-tape test (splitting resistance).

For this purpose, an adhesive strip was adhered firmly and without bubbles to the surface. This adhesive strip was then peeled off again, so that the substrate was not damaged. The splitting resistance was assessed on the basis of a rating system, visually, from rating 1 (very good) to rating 5 (very poor). A poor splitting resistance is reflected in a correspondingly high level of extraction from the print.

It was found that the inventive brass pigments from example 15 had a better adhesive strength (rating 2) than the gold-bronze pigments from comparative example 17 (rating 4) and the PVD aluminum pigments from comparative example 18 (rating 3).

When the experimental results are viewed as a whole, it is notable that the inventive pigments exhibit pigment characteristics, particularly in respect of thickness, thickness distribution, and opacity, that have not hitherto been achieved with conventional leafing gold-bronze pigments produced by dry grinding. The reverse film applications pigmented with inventive pigments are notable for attractive coloristic properties, especially for a gold mirror effect with a high color density, which it has not hitherto been possible to achieve with PVD aluminum pigments containing color pigments. Reverse film applications pigmented with inventive pigments possess a high adhesive strength. Moreover, as a result of the high opacity of the pigments of the invention, it is possible to reduce the amount in which they are used in the application medium.

C PVD EFFECT PIGMENT EXAMPLES

Example 19

400 g of a commercial PVD pigment (Metalure L55700, Eckart) were introduced with 2 g of the additive from example 1a into a mill according to example 1b with 6.5 kg of steel balls (diameter 0.8 mm), and the mill was sealed. The mixture was ground at 30 rpm for 3 h. The ground product was separated from the grinding media and adjusted to a solids content of 10%.

Comparative Example 20

Grinding as in example 19, but using an lubricant 2 g of a customary mixture of stearic and oleic acid.

Comparative Example 21

Commercially available PVD pigment Metalure L (Eckart GmbH), treated as per example 19 but without any addition of lubricant or additive, in a mill.

Characterization took place in accordance with the methods already described above.

Particle size, gloss (gravure (NC, acrylate), mirror), splitting resistance

TABLE 8

Characterization of the pigments

| Sample | Lubricant | Particle size distribution | | Testing gravure ink nitrocellulose; level of pigmentation: 3.8% | | Testing mirror application level of pigmentation: 3.8% |
| --- | --- | --- | --- | --- | --- | --- |
| | | $d_{50}/\mu m$ start | $d_{50}/\mu m$ end | Gloss 60° | Hiding | Gloss 60° |
| Example 19 | Example 1a | 11.3 | 8.2 | 274 | good (2) | 497 |
| Comparative example 20 | Stearic/ oleic acid mixture | 11.3 | 10.8 | 258 | moderate (3) | 469 |
| Comparative example 21 | — | 11.3 | 10.1 | 208 | low (5) | 480 |

Example 22

Commercially available PVD pigment (Metalure L, Eckart) was combined with 3% of an additive from example 1a, and processed further to give a metallic effect pigment paste.

Comparative example 23

Commercially available PVD pigment (Metalure L, Eckart) without addition of additive.

TABLE 9

Characterization of the pigments

| Sample | Additive | Testing gravure ink nitrocellulose; level of pigmentation: 3.8% | | Testing mirror coating application; level of pigmentation: 3.8% |
| --- | --- | --- | --- | --- |
| | | Gloss 60° | Hiding | Gloss 60° |
| Example 22 | Example 1a | 297 | very good (1) | 527 |
| Comparative example 23 | — | 292 | good (2) | 510 |

The examples recited showed an improvement in the optical properties even of PVD pigments as a result of the inventive additives or lubricants and their use after or during grinding.

Where the PVD pigments were ground with the additives, there was a reduction in the average size ($d_{50}$). In spite of this particle size reduction, the gloss of the pigment in the gravure ink and in the mirror coating application is improved. PVD pigments with lower particle sizes are advantageous for certain applications such as, for example, gravure printing inks.

What is claimed is:

1. A metallic effect pigment, selected from the group consisting of aluminum, copper and gold bronze, wherein the metallic effect pigment is platelet-shaped, and having an average size/thickness ratio (form factor) of at least 5:1, with an additive, said pigment and additive together forming a metallic effect pigment composition, wherein the additive is applied at least partly on the metallic effect pigment such that 0.2% to 5% by weight of additive, based on the amount of metallic effect pigment and additive, is bound on a surface of the metallic effect pigment, and wherein the additive comprises as structural units at least one carboxylic acid having at least four carbon atoms, and also at least one polyglycol ether, wherein the carboxylic acid and the polyglycol ether are bonded covalently to one another, wherein the metallic effect pigment is a platelet-shaped metallic pigment having a metal core, wherein the metallic effect pigment composition is in the form of a metal effect pigment paste or a metal effect pigment powder, wherein the metallic effect pigment is obtained by dry grinding or wet grinding of atomized metal powder and wherein where the pigment is obtained by wet grinding, the wet grinding is carried out in organic solvents.

2. The metallic effect pigment composition of claim 1, wherein the carboxylic acid and the polyglycol ether are covalently bonded to one another via an ester bond or an amide bond.

3. The metallic effect pigment composition of claim 1, wherein the carboxylic acid is at least one polycarboxylic acid having two to eight carboxylic acid groups.

4. The metallic effect pigment composition of claim 3, wherein the polycarboxylic acid is a dimerized, trimerized or tetramerized fatty acid or mixtures of these forms.

5. The metallic effect pigment composition of claim 3, wherein the polycarboxylic acid contains 10 to 96 carbon atoms.

6. The metallic effect pigment composition of claim 5, wherein the polycarboxylic acid contains 12 to 76 carbon atoms.

7. The metallic effect pigment composition of claim 1, wherein the carboxylic acid is saturated or unsaturated.

8. The metallic effect pigment composition of claim 1 wherein the polyglycol ether comprises a group $R^1$—X—$(R^2$—O$)_y$—$(R^3$—O$)_z$—$(R^4$—O$)_k$—, where the $R^2$—O, $R^3$—O, and $R^4$—O polyether units may be arranged randomly, alternately or as block copolymers, X is O, S, (CO)O or $NR^x$, where $R^x$ is H or an aliphatic radical having 1 to 20 carbon atoms, and $R^1$ is a linear or branched aliphatic radical or araliphatic or aromatic organic radical having 1 to 30 carbon atoms, and $R^2$, $R^3$ and $R^4$ may be identical or, independently of one another, different and are each a linear or branched aliphatic organic radical or araliphatic or aromatic organic radical having 1 to 12 carbon atoms, and y, z, and k are natural numbers and independently of one another are 0 to 200, with the proviso that y+z+k=2 to 600.

9. The metallic effect pigment composition of claim 8, wherein the ratio of the number of ether units y+z+k to the number of C atoms of the carboxylic acid or of the polycarboxylic acid and also, of the aliphatic or araliphatic radical $R^1$, and of the aliphatic radical $R^x$, amounts to values of 0.1 to 4.0.

10. The metallic effect pigment composition of claim 1, wherein the carboxylic acid is partly or wholly esterified.

11. The metallic effect pigment composition of claim 10, wherein the carboxylic acid is partly esterified and the additive has an acid number of 5 to 140 mg KOH/g additive.

12. The metallic effect pigment composition of claim 1, wherein the carboxylic acid is present partly or wholly as carboxylic acid salt.

13. The metallic effect pigment composition of claim 1, wherein the metallic effect pigments are in compacted form.

14. The metallic effect pigment composition of claim 13, wherein the compacted form is selected from the group consisting of granules, pellets, tablets, briquettes, sausages and paste.

15. A method for producing the metallic effect pigment of claim 1, wherein the method comprises the following steps:
   a) grinding metal particles to metallic effect pigments in the presence of an additive which comprises as structural units at least one carboxylic acid having at least 4 carbon atoms, and also at least one polyglycol ether, wherein the carboxylic acid and the polyglycol ether are bonded covalently to one another, and grinding media and also, optionally, a liquid phase,
   b) separating the metallic effect pigments obtained in step a) and provided with the additive from the grinding media and optionally from the liquid phase,
   c) optionally compacting the metallic effect pigments separated in step b) and provided with the additive.

16. The method of claim 15, wherein step a) is carried out in a ball mill in the presence of grinding media.

17. The method of claim 16, wherein the grinding media is spherical grinding media.

18. The method of claim 15, wherein the compacting is carried out by at least one of granulating, pelletizing, tableting, briquetting, filtering, pressing and extruding.

19. A coating composition comprising the metallic effect pigment composition of claim 1.

20. The coating composition of claim 19, wherein the coating composition is a printing ink.

21. The metallic effect pigment composition of claim 1, having an average thickness $h_{50}$ in a range of 20 nm to 2 μm.

22. The metallic effect composition of claim 1, having an average thickness $h_{50}$ in a range of 20 nm to 100 nm.

23. The metallic effect pigment composition of claim 1, having an average size $d_{50}$ in the range of 3 to 100 μm.

24. The metallic effect pigment composition of claim 1, having an average size/thickness ratio (form factor) of at least 50:1.

\* \* \* \* \*